United States Patent [19]

Scott

[11] Patent Number: 4,579,112

[45] Date of Patent: Apr. 1, 1986

[54] FOAM EARPLUG

[76] Inventor: Robert T. Scott, 416 Lighthouse Ave., Santa Cruz, Calif. 95060

[21] Appl. No.: 611,158

[22] Filed: May 17, 1984

[51] Int. Cl.⁴ ............................................. A61F 11/00
[52] U.S. Cl. .................................................... 128/151
[58] Field of Search ................................. 128/151, 152

[56] References Cited

U.S. PATENT DOCUMENTS 2,538,339  1/1951  Thomas ................................ 128/152
3,811,437  5/1974  Gardner, Jr. ......................... 128/152

FOREIGN PATENT DOCUMENTS 183171     9/1955  Austria ................................. 128/151
1947740    5/1971  Fed. Rep. of Germany ...... 128/152
WO82/01312 4/1982  PCT Int'l Appl. .................. 128/151

Primary Examiner—Mark L. Bell

[57] ABSTRACT

An earplug is provided which does not enter the ear canal but which merely blocks the entrance of the canal. The plug is made of a closed cell elastomeric foam having a tear drop elipsoid shape when viewed from above and a rectangular shape when viewed from the side. The plug is slightly compressed and placed in a blocking position behind the tragus.

3 Claims, 7 Drawing Figures

FOAM EARPLUG

SUMMARY OF THE INVENTION

The external ear canal opening or meatus is rectangular. A cylinder with tear drop elipsoid cross-section of soft foam when oriented with its long axis in the vertical outlines a rectangular shape. When gently squeezed into place behind the tragus such a soft cylinder of foam blocks the external ear canal without deeply penetrating the external ear canal. A very good seal of plug against skin is obtained as the memory of the foam material causes a constant expansion outward. The near airtight seal affords marked attenuation of sound by blocking air conduction. Further attenuation of sound results from the convex surface which reflects sound waves away from the external ear canal. This convex surface reverses the focusing and resonating effects on the funnel (concave) shape of the pinna. The foam material with its 99% closed cell structure helps exhaust the energy of sound as the waves are bounced through the hundreds of individual cells changing directions thousands of times. The sound waves are scattered in thousands of directions as the impulses are reflected off the convex and concave air cell walls in the foam. Sound energy in decibels (dB) is thus exhausted markedly. The tear drop elipsoid cross-section permits fitting of the one sized cylinder to a nearly unlimited variety of meatal outlines and sizes.

The plug of the present invention is primarily adapted for use in sound attenuation to protect the inner ear cochlea from excessive noise in industry, including exposure to jet engine noise and gunfire. This design and use of an earplug can also be used to keep most water out of the ear canal, so it may be used by swimmers, surfers and the like.

The earplug of the present invention which rests in the cavum conchae is less irritating to that particular skin than an earplug in contact with the more sensitive skin covering the external ear canal. A much longer comfortable wearing time is made possible lending itself to the length of a normal working day. It is also well tolerated when used by light sleepers.

The earplug will not impact ear wax into the depths of the external ear canal as happens with any earplug which penetrates the external ear canal. The loss of ear wax from the skin of the external ear canal compromises the skin and makes it more prone to infection and inflammation (external otitis). The pressure of a penetrating earplug against the skin causes ischemia which leads to the breakdown of the skin.

DESCRIPTION OF THE PREFERRED EMBODIMENT

Figure 3:
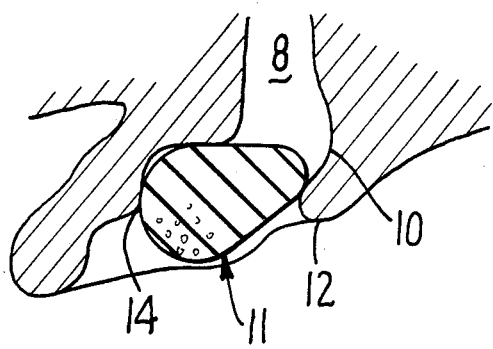
FIG. 3 is a section on the line 3—3 of FIG. 2.
Figure 1:
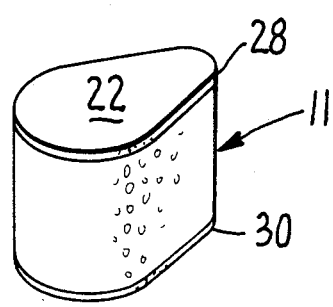
FIG. 1 is a perspective view of an earplug embodying the present invention.

Referring to the drawings by reference characters, the external ear canal generally designated 8 extends inwardly from the choncha 10. The opening to the auditory canal is generally rectangular and is roughly defined by the space between the tragus 12 and the antihelix 14. It is the object of the present invention to provide an earplug which blocks this generally rectangular opening to the auditory canal without actually entering the canal in the manner of previous earplugs.

Figure 5:
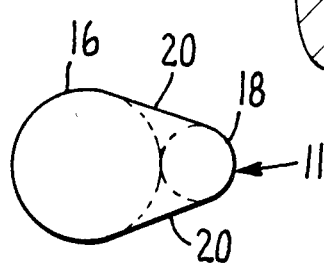
FIG. 5 is a plan or top view of a plug embodying the present invention.
Figure 6:
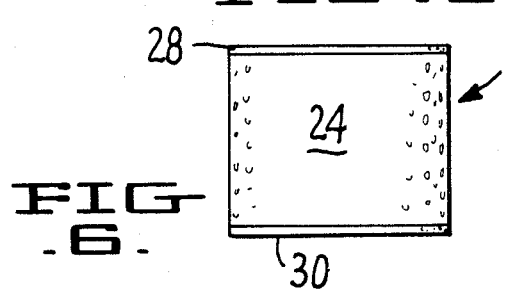
FIG. 6 is a side view of the plug.
Figure 7:
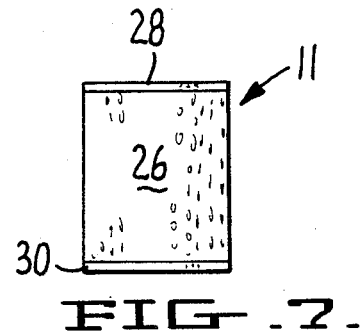
FIG. 7 is an end view of the plug.

The earplug of the present invention is generally designated 11 and has a shape which in plan or from the top would be described as a tear drop elipsoidal cross-section. Thus, referring to FIG. 5, the top shape can be generated by two imaginary circles designated 16 and 18 with sides 20 forming tangents connecting the two circles. Circle 16 is about twice the diameter of circle 18. Thus, the top 22 appears as a tear drop while the side 24 appears as a square while the end 26 is in the shape of a rectangle.

Figure 2:
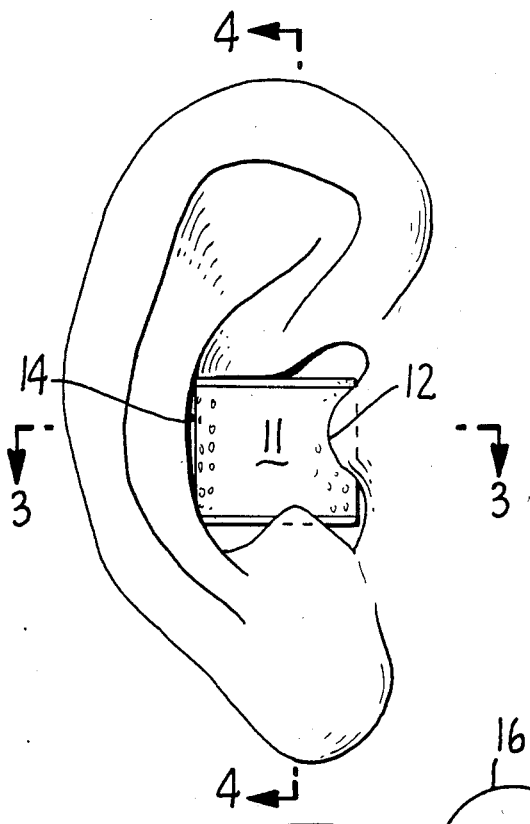
FIG. 2 is a side view of an ear with an earplug embodying the present invention in place.
Figure 4:
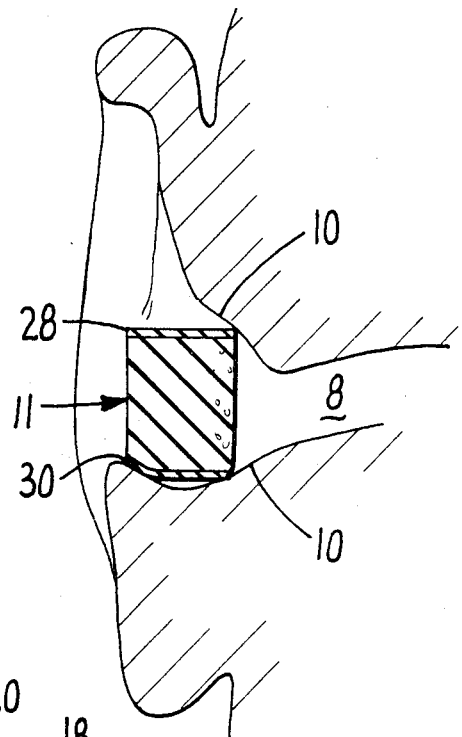
FIG. 4 is a section on the line 4—4 of FIG. 2.

In use, the earplug is merely held in an upright position with the smaller end toward the tragus and pushed into the pinna where the plug is compressed only slightly as is shown in FIG. 2. As is shown in FIGS. 3 and 4, the plug completely blocks the external ear canal but does not substantially enter the canal. Thus, the plug of the present invention does not impact ear wax into the depths of the canal nor does it cause the loss of ear wax when it is removed.

In accordance with one embodiment of the invention, the top and bottom of the plug are provided with a coating of an impervious material, such as sheet rubber, as at 28 and 30. However, this is not necessary to the operation of the plug.

The plug itself is made of a closed cell elastomeric foam which can be a natural or synthetic rubber. The foam is soft and easily compressible and has a memory, so that when it is compressed slightly, it will tend to spring back holding the plug securely in place.

Although a specific embodiment of the invention has been shown and described, it will be obvious skilled in the art that many variations can be made in the exact structure shown.

I claim:

1. An earplug made of an elastomeric closed cell foam, said earplug having a tear drop elipsoid shape when viewed from above, a rectangular shape when viewed from the end and a square shape when viewed from the side, said plug being adapted to be lightly compressed and placed in a blocking position behind the tragus without penetrating the external ear canal.

2. The earplug of claim 1 wherein the tear drop elipsoid shape is generated by two imaginary side-by-side circles, one of which is about twice the diameter of the other with straight side members lying tangent to the two circles.

3. The earplug of claim 1 wherein the top and bottom of the plug are covered with an impervious material.

* * * * *